(12) United States Patent
Belcher

(10) Patent No.: US 8,152,853 B2
(45) Date of Patent: Apr. 10, 2012

(54) KNEE PROSTHESIS WITH ROTATABLE POST

(75) Inventor: Nathan E. Belcher, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 231 days.

(21) Appl. No.: 12/479,148

(22) Filed: Jun. 5, 2009

(65) Prior Publication Data

US 2010/0312351 A1 Dec. 9, 2010

(51) Int. Cl.
*A61F 2/38* (2006.01)

(52) U.S. Cl. ............... 623/20.33; 623/20.32; 623/20.34; 623/20.14

(58) Field of Classification Search .... 623/20.32–20.34, 623/20.14; *A61F 2/38*
See application file for complete search history.

(56) References Cited

U.S. PATENT DOCUMENTS

| | | | |
|---|---|---|---|
| 3,869,729 A | 3/1975 | Attenborough |
| 4,224,697 A | 9/1980 | Murray et al. |
| 4,790,853 A | 12/1988 | Engelbrecht et al. |
| 4,950,297 A | 8/1990 | Elloy et al. |
| 5,116,376 A | 5/1992 | May |
| 5,139,521 A | 8/1992 | Schelhas |
| 5,314,483 A | 5/1994 | Wehrli et al. |
| 5,370,701 A | 12/1994 | Finn |
| 5,702,466 A | 12/1997 | Pappas et al. |
| 5,755,804 A | 5/1998 | Schmotzer et al. |
| 5,824,102 A | 10/1998 | Buscayret |
| 6,019,794 A | 2/2000 | Walker |
| 6,039,764 A | 3/2000 | Pottenger et al. |
| 6,080,195 A | 6/2000 | Colleran et al. |
| 6,099,570 A | 8/2000 | Livet et al. |
| 6,117,175 A | 9/2000 | Bosredon |
| 6,210,444 B1 | 4/2001 | Webster et al. |
| 6,210,445 B1 | 4/2001 | Zawadzki |
| 6,217,618 B1 | 4/2001 | Hileman |
| 6,986,791 B1 | 1/2006 | Metzger |

OTHER PUBLICATIONS

Vanguard™ SSK Revision System—Surgical Technique, Biomet® Orthopedics, 2008.
Vanguard® SSK Revision System, 2009.

*Primary Examiner* — Thomas J Sweet
*Assistant Examiner* — Jason-Dennis Stewart
(74) *Attorney, Agent, or Firm* — Harness, Dickey

(57) ABSTRACT

A knee joint prosthesis for implantation to replace a portion of a knee joint. The knee joint prosthesis includes a tibial tray and a bearing member that engages the tibial tray. The prosthesis also includes an insert with a base that is fixed to the bearing member and an extension portion that extends away from the bearing member and the tibial tray. The extension portion has an axis, and the extension portion includes a threaded portion. The prosthesis further includes a post that is rotatably coupled to the extension portion, and the post is rotatable about the axis of the extension portion relative to the insert. Furthermore, the prosthesis includes a retention member that threadably couples to the threaded portion of the insert to limit movement of the post along the axis away from the bearing member and the tibial tray.

19 Claims, 7 Drawing Sheets

KNEE PROSTHESIS WITH ROTATABLE POST

FIELD

The following relates to a knee prosthesis and, more particularly, to a knee prosthesis with a rotatable post.

BACKGROUND

The statements in this section merely provide background information related to the present disclosure and may not constitute prior art.

The human anatomy includes many articulating joints. For example, the femur and tibia cooperate to form a knee joint of the human anatomy and articulate to allow ease of walking and mobility. Nevertheless, over time, disease and injury may deteriorate the knee joint, such that articulation of the joint becomes painful or impractical. When such deformities or injuries occur, anatomical replacements, particularly implants and prosthetics, can be placed in the femur or the tibia, or both to replace the damaged portions and restore the natural articulation of the knee joint.

However, replacing only the articulating portions is not always practical or possible. Particularly, certain tissues such as the anterior cruciate ligament, the posterior cruciate ligament, tendons, and muscles may not be able to withstand natural loading of the joint, even if the articulating portions of the joint are replaced by prosthetic members. Thus, the prosthetic knee may need to also replace and/or compensate for those tissues.

One exemplary component of this type of prosthetic knee is a posterior stabilized prosthetic knee joint. The posterior stabilized knee prosthetic may include a post, particularly a posterior stabilized (PS) post, which extends superiorly from a tibial component to operably engage a femoral component, or the anatomical femur, to constrain posterior movement of the knee, which is not otherwise able to be constrained by the anatomical soft tissues. Improvements of this type of prosthetic knee are desired.

SUMMARY

A knee joint prosthesis for implantation to replace a portion of a knee joint is disclosed. The knee joint prosthesis includes a tibial tray and a bearing member that engages the tibial tray. The prosthesis also includes an insert with a base that is fixed to the bearing member and an extension portion that extends away from the bearing member and the tibial tray. The extension portion has an axis, and the extension portion includes a threaded portion. The prosthesis further includes a post that is rotatably coupled to the extension portion, and the post is rotatable about the axis of the extension portion relative to the insert. Furthermore, the prosthesis includes a retention member that threadably couples to the threaded portion of the insert to limit movement of the post along the axis away from the bearing member and the tibial tray.

In another aspect, a knee joint prosthesis for implantation to replace a portion of a knee joint is disclosed. The knee joint prosthesis includes a tibial tray and bearing member that engages the tibial tray. The bearing member includes a tray engaging surface that engages the tibial tray. The knee joint prosthesis additionally includes a post and an insert with a base that is fixed to the bearing member and an extension portion that extends away from the bearing member and the tibial tray. The post is rotatably coupled to the extension portion to be rotatable about an axis of the extension portion, and the post is limited against movement along the axis away from the bearing member and the tibial tray. The base includes an inferior terminal end that is disposed superior to the tray engaging surface of the bearing member.

Additionally, a knee joint prosthesis for implantation to replace a portion of the knee joint is disclosed. The knee joint prosthesis includes a tibial component having a tibial tray with a bearing engaging surface and a bearing member that is fixed to the tibial tray to be disposed adjacent the bearing engaging surface of the tibial tray. The bearing member also includes a tray engaging surface that engages the tibial tray. Furthermore, the tibial component includes an insert with a base that is embedded within the bearing member to be fixed to the bearing member. The base includes an inferior terminal end that is disposed superior to the tray engaging surface of the bearing member. The insert further includes an extension portion that extends away from the bearing member and the tibial tray. The extension portion has an axis, and the extension portion includes a threaded portion. Furthermore, the tibial component includes a post having a bore and counterbore that receive the extension portion to rotatably couple the post to the extension portion for rotation about the axis relative to the insert. Additionally, the tibial component includes a washer that is disposed between the post and the bearing member, and the washer inhibits wear due to rotation of the post relative to the bearing member. Also, the tibial component includes a nut that receives the extension portion to threadably couple to the threaded portion of the extension portion and to limit movement of the post along the axis away from the bearing member and the tibial tray. The nut is received within the counterbore of the post. Moreover, the tibial component includes a weldment that bonds the retention member to the insert. Still further, the knee joint prosthesis includes a femoral component with an inferior portion having an opening. The inferior portion is coupled for articulation on the bearing member, and the post is moveably received within the opening.

Moreover, a method of assembling a knee joint prosthesis for replacing a portion of a knee joint is disclosed. The method includes engaging a bearing member with a tibial tray. The bearing member has an insert insert-molded therein with a base embedded within the bearing member. An inferior terminal end of the insert is disposed superior to a tray engaging surface of the bearing member, and an extension portion of the insert extends away from the bearing member. The method further includes rotatably coupling a post to the extension portion for rotation of the post about an axis of the extension portion. Additionally, the method includes threadably coupling a retention member to the extension portion to limit movement of the post along the axis away from the bearing member. Still further, the method includes coupling a femoral component for articulation on the bearing member, wherein the post is moveably received within an opening of the femoral component.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
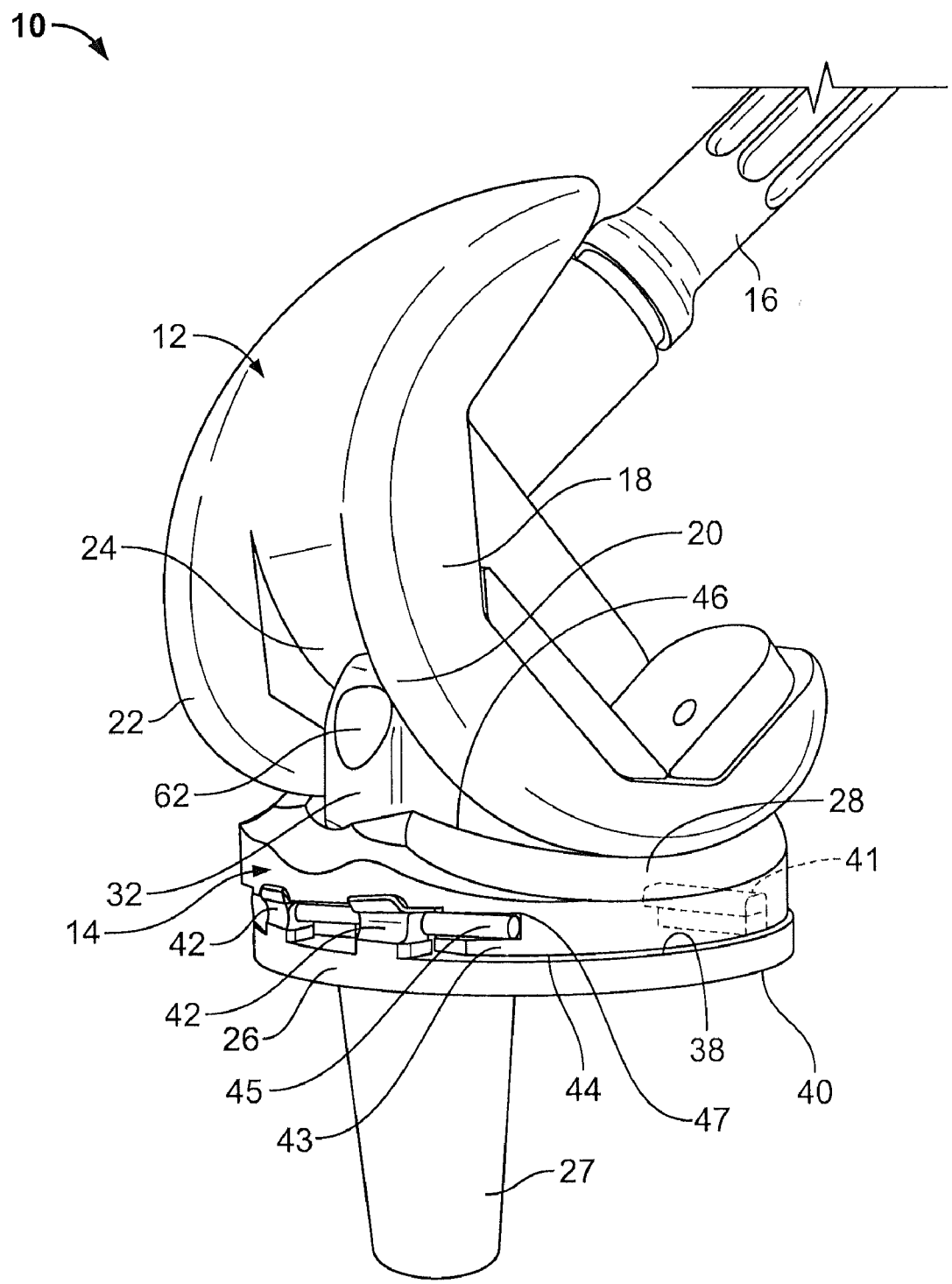
FIG. 1 is a perspective view of an exemplary embodiment of a knee joint prosthesis according various teachings of the present disclosure.

The following description is merely exemplary in nature and is not intended to limit the present disclosure, application, or uses. It should be understood that throughout the drawings, corresponding reference numerals indicate like or corresponding parts and features.

Referring initially to FIG. 1, a knee joint prosthesis 10 according to various exemplary embodiments is illustrated. The knee joint prosthesis 10 can be implanted within a patient to replace at least a portion of a knee joint. Generally, the knee joint prosthesis 10 can include a femoral component 12 and a tibial component 14. The femoral and tibial components 12, 14 are coupled for articulation, as will be discussed in greater detail below, to emulate an anatomical knee joint.

The knee joint prosthesis 10 can incorporate one or more features of the commercially available VANGUARD® SSK Revision System of Biomet, Inc., located in Warsaw, Ind. In some embodiments, the knee joint prosthesis 10 can be a posterior stabilized knee prosthetic; however, it will be appreciated that the prosthesis 10 can be of any suitable type without departing from the scope of the present disclosure. Furthermore, it will be appreciated that the knee joint prosthesis 10 can include only the tibial component 14 coupled to an anatomical femur (not shown).

As shown in FIG. 1, the femoral component 12 can include a stem 16. The stem 16 can be axially straight and generally cylindrical to be received within and fixed to a resected femur (not shown). It will be appreciated that the stem 16 can be optionally included within the prosthesis 10. For instance, the femoral component 12 can be adapted for a fully constrained knee joint prosthetic that includes the stem 16. The femoral component 12 can also be adapted for a posterior stabilized knee joint prosthetic that does not include the stem 16.

Furthermore, the femoral component 12 can include an inferior portion 18, which is fixed to the stem 16. The inferior portion 18 can include a first condyle 20 and a second condyle 22. Furthermore, the inferior portion 18 can include an opening 24 (i.e., an inter-condylar box), which is defined between the first and second condyles 20, 22. It will be appreciated that the inferior portion 18 could include only the first condyle 20 or the second condyle 22 with remaining portions of the femur being anatomical bone.

The tibial component 14 can include a tibial tray 26 having a tibial stem 27. The tibial stem 27 can be elongate and frusto-conical in shape and can be received within and affixed to a resected tibia bone (not shown). The tibial component 14 can further include a bearing member 28 that engages the tibial tray 26 to be disposed adjacent and supported by the tibial tray 26. In addition, the tibial component 14 can include an insert 30 (FIGS. 2, 6, and 8) that is partially embedded and fixed against rotation within the bearing member 28. The tibial component 14 can also include a post 32 (FIGS. 1 and 2) that is rotatably coupled to the insert 30. Furthermore, the tibial component 14 can include a washer 34 (FIGS. 2 and 9) that is disposed between the bearing member 28 and the post 32. The tibial component 14 can include a retention member 36 (FIGS. 2, 3A, 3B, 7, and 8) that is fixed to the insert 30 and that limits movement of the post 32 in a direction generally away (i.e., superiorly) from the bearing member 28 and the tibial tray 26, as will be discussed in greater detail below. As will be discussed, the tibial component 14 facilitates assembly of the knee joint prosthesis 10, and the tibial component 14 includes various features that make the knee joint prosthesis 10 more robust.

As shown in FIG. 1, the tibial tray 26 can include a superior surface 38 (i.e., a bearing engaging surface) that is substantially flat. The tibial tray 26 can also include an inferior surface 40 that is opposite to the superior surface 38. The stem 27 can be fixed to and can extend inferiorly from the inferior surface 40. It will be appreciated that the inferior surface 40 can abut and can be supported by a resected tibia (not shown). Furthermore, the tibial tray 26 can include one or more anterior projections 42 that extend superiorly from the superior surface 38. The tibial tray 26 can also include one or more posterior projections 41 (FIGS. 1 and 11) that extend superiorly from the superior surface 38. The tibial tray 26 can be made out of any suitable material, such as a metal (e.g., cobalt, cobalt alloy, etc). It will be appreciated that the tibial tray 26 can be suitable for accommodating a cruciate retaining (CR) prosthetic, a posterior stabilized (PS) prosthetic, or a fully constrained (FC) prosthetic. Accordingly, the tibial tray 26 need not be adapted specifically for the knee joint prosthesis 10 of the present disclosure. Furthermore, it will be appreciated that the tibial tray 26 can be of a type included in the commercially available VANGUARD® 360 system or the REGENEREX® system of Biomet, Inc. located in Warsaw, Ind.

Also, as shown in FIGS. 1, 2, 3A, 3B, and 4, the bearing member 28 can include an inferior surface 44 (i.e., a tray engaging surface) that is substantially flat (FIGS. 1, 2-4, and 11). The inferior surface 44 can be a surface located furthest in the inferior direction. The bearing member 28 can also include one or more anterior projections 43 (FIGS. 1, 3B, and 11) that extend in an anterior direction from the bearing member 28.

Figure 11:
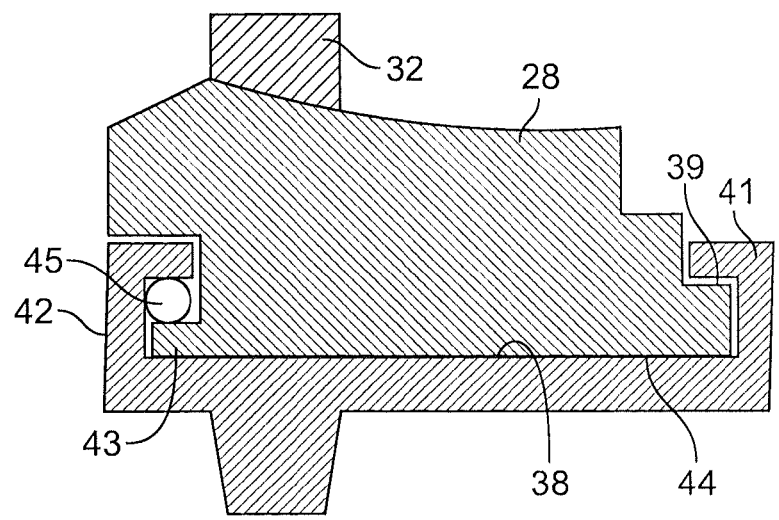
FIG. 11 is a cross sectional view of the tibial component of the knee joint prosthesis of FIG. 1.

The bearing member 28 can engage the tibial tray 26 in any suitable fashion. For instance, as shown in FIG. 11, the bearing member 28 can be fixed to the tibial tray 26 such that the inferior surface 44 of the bearing member 28 engages, abuts, and is supported by the superior surface 38 of the tibial tray 26. Furthermore, the knee joint prosthesis 10 can include an engagement member 45 (FIG. 1), which is elongate. As shown in FIGS. 1 and 11, the engagement member 45 can be received within a recess 47 defined between the anterior projections 42, 43 of the tibial tray 26 and bearing member 28, respectively, and the engagement member 45 can fixedly engage the bearing member 28 to the tibial tray 26. Furthermore, the posterior projection 41 of the tibial tray 26 can hook onto and retain a superior posterior surface 39 to further fix the bearing member 28 to the tibial tray 26.

Moreover, the bearing member 28 can include a superior surface 46, which is non-planar. The superior surface 46 can include a plurality of rounded articulation recesses 48a, 48b. As shown in FIG. 1, the articulation recesses 48a, 48b can receive the first and second condyles 20, 22 of the femoral component 12, respectively, such that the first and second condyles 20, 22 can articulate on the bearing member 28. Also, a central recess 50 can be defined between the articulation recesses 48a, 48b.

The bearing member 28 can be made out of any suitable material. For instance, the bearing member 28 can be made out of a polymer, such as ultra-high molecular weight polyethylene (UHMWPE). As such, the bearing member 28 can allow the femoral component 12 to articulate on the bearing member 28 with relatively low wear.

Figure 2:
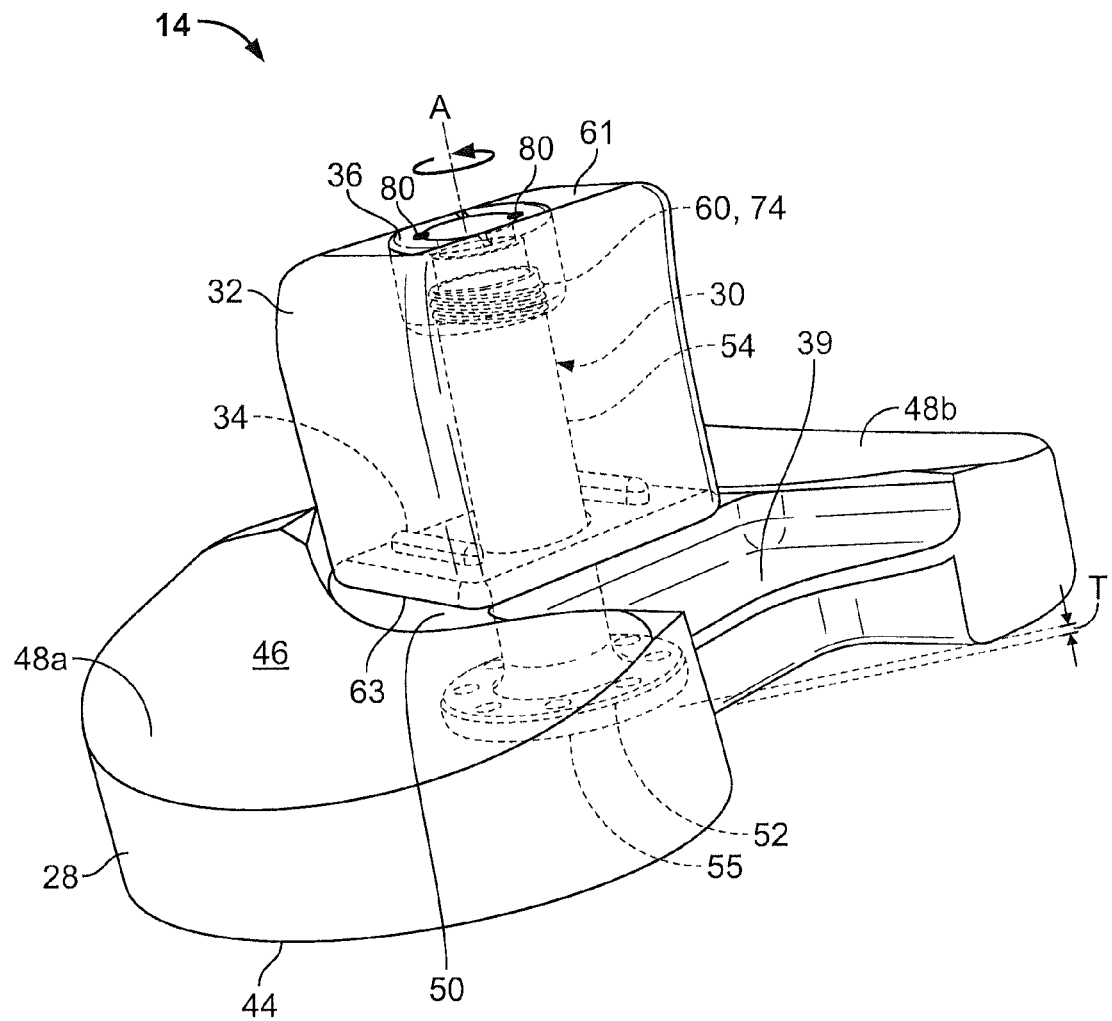
FIG. 2 is a perspective view of a tibial component of the knee joint prosthesis of FIG. 1.
Figure 3A:
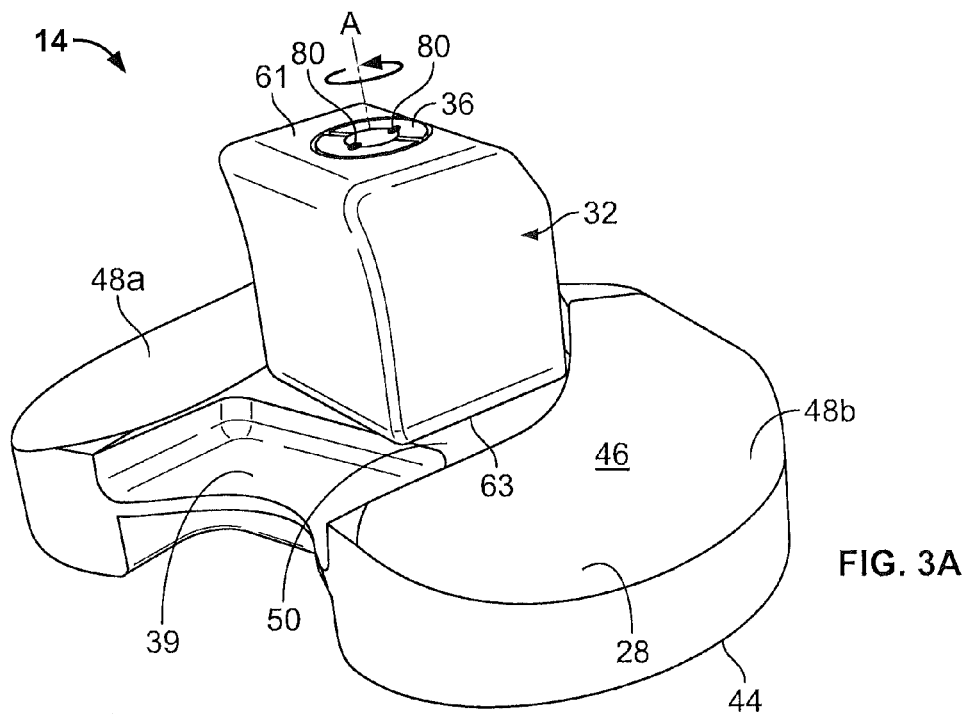
FIGS. 3A and 3B are perspective views of the tibial component of the knee joint prosthesis of FIG. 1.
Figure 3B:
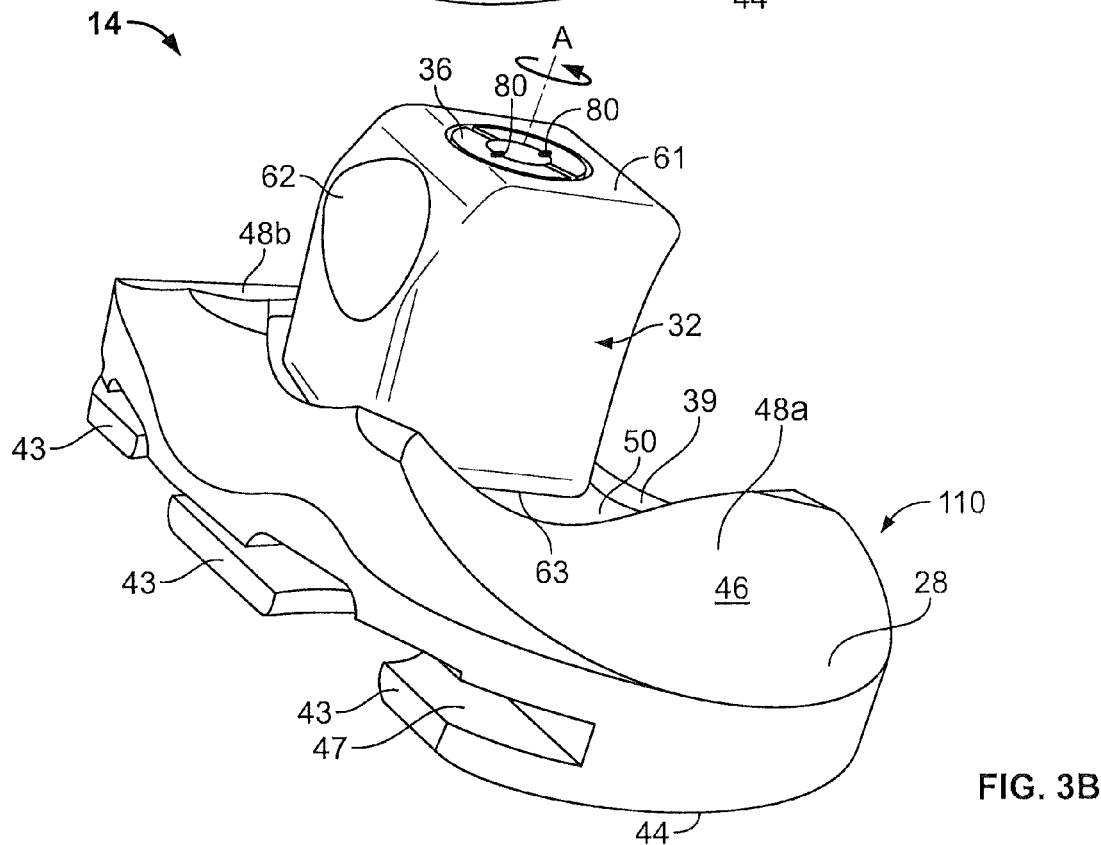
Figure 4:
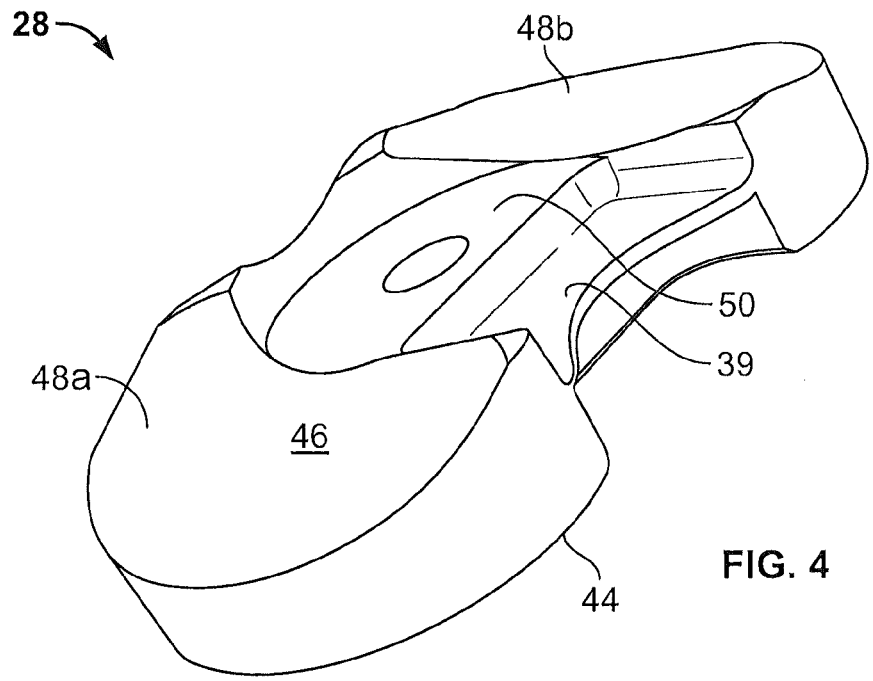
FIG. 4 is a perspective view of a bearing member of the knee joint prosthesis of FIG. 1.
Figure 5:
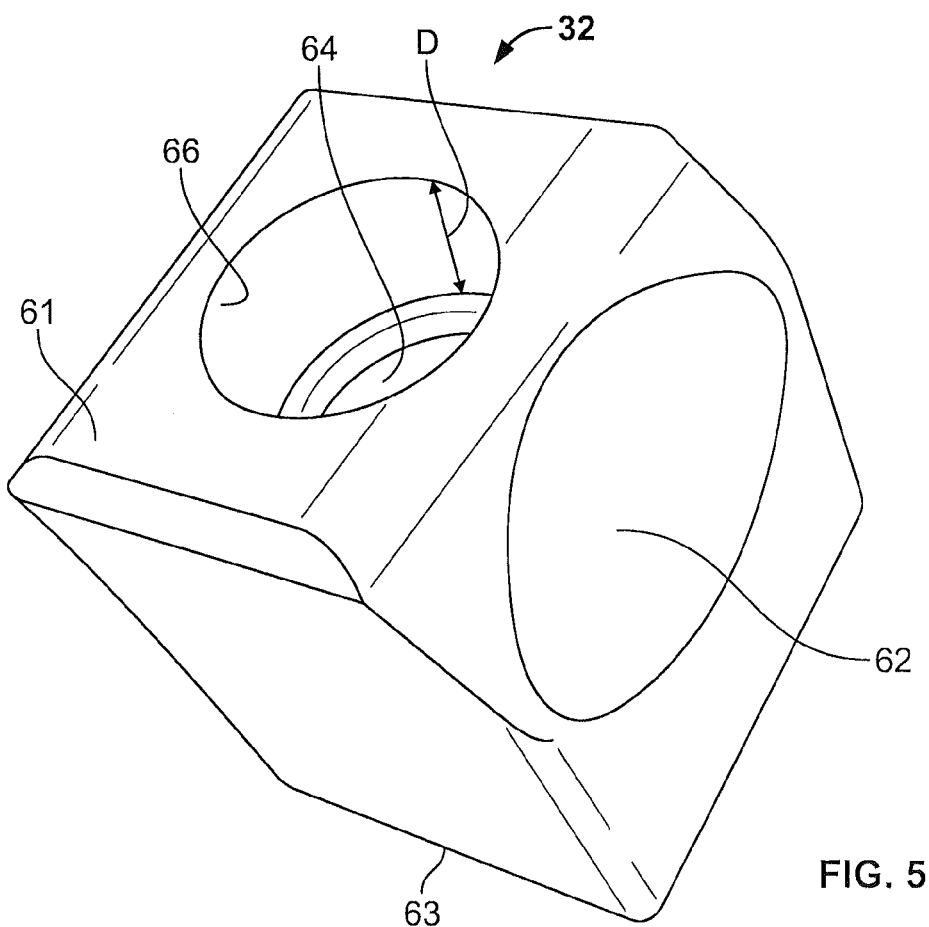
FIG. 5 is a perspective view of a post of the knee joint prosthesis of FIG. 1.
Figure 6:
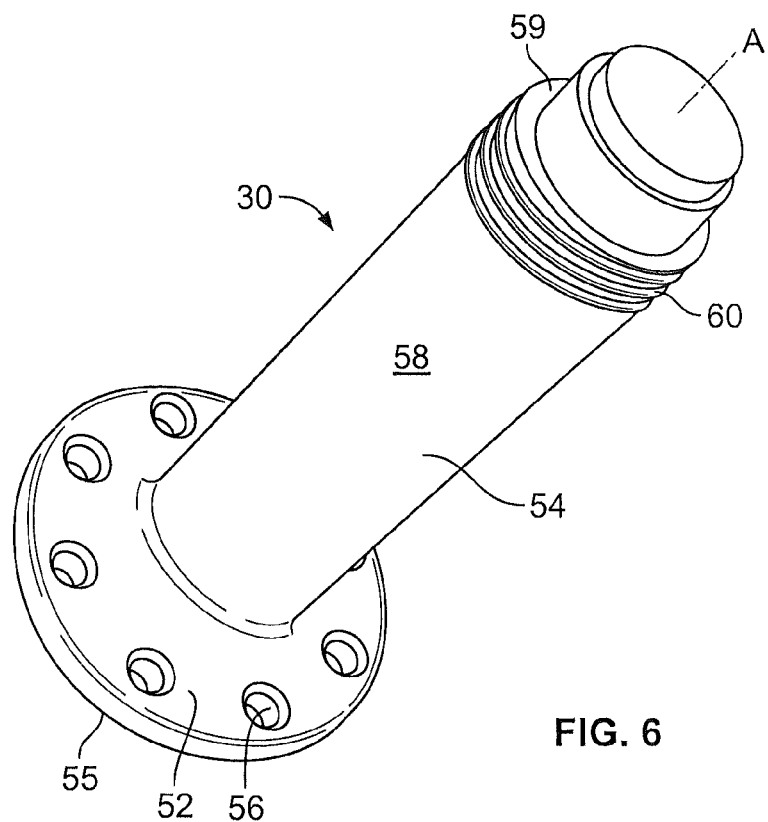
FIG. 6 is a perspective view of an insert of the knee joint prosthesis of FIG. 1.
Figure 7:
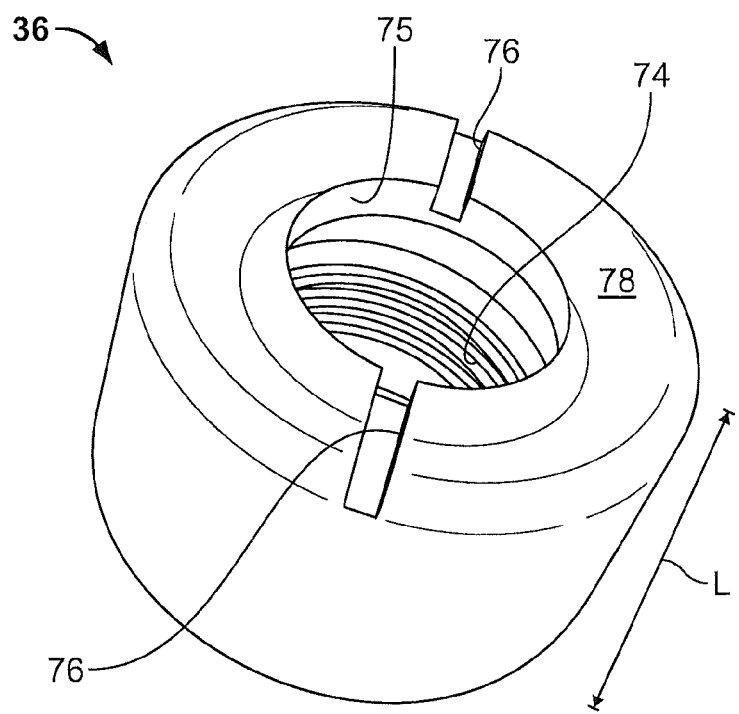
FIG. 7 is a perspective view of a retention member of the knee joint prosthesis of FIG. 1.
Figure 8:
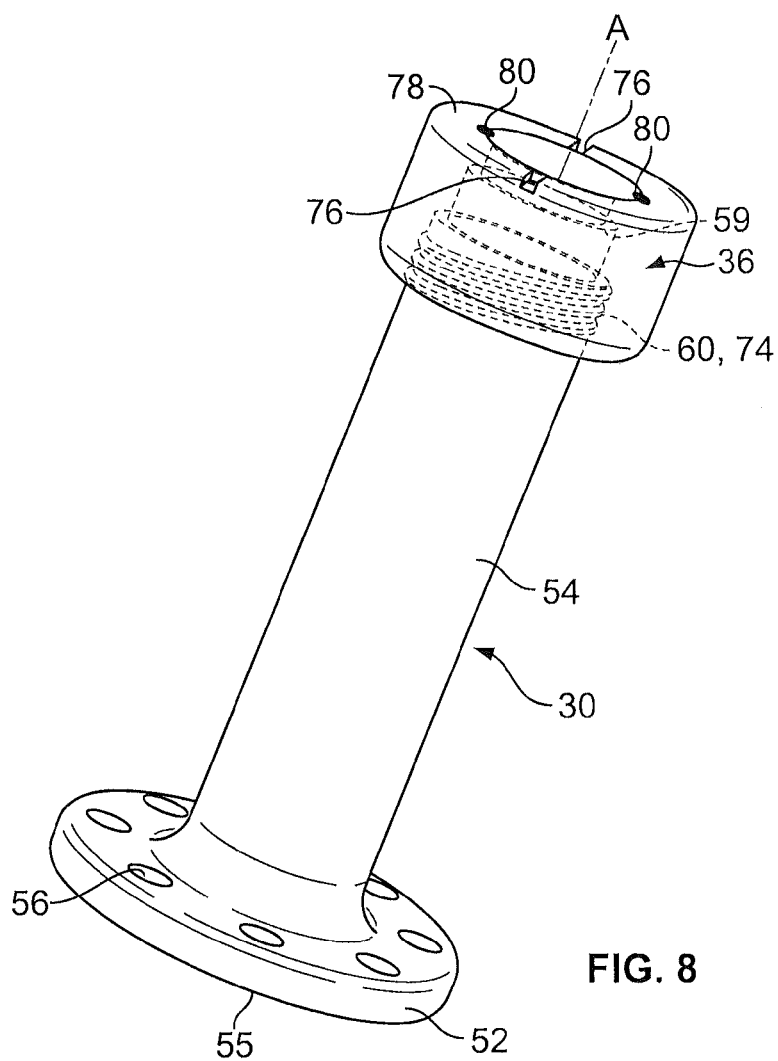
FIG. 8 is a perspective view of the insert and the retention member of the knee joint prosthesis of FIG. 1.

In addition, as shown in FIGS. 2, 6 and 8, the insert 30 can include a base 52, which is fixed to the bearing member 28. The insert 30 can include an extension portion 54, which extends away from and is exposed from the bearing member 28. The base 52 and the extension portion 54 of the insert 30 can be integrally attached so as to be monolithic; however, the base 52 and the extension portion 54 can be removably coupled in some embodiments. The extension portion 54 can define an axis A. Moreover, the insert 30 can be made out of any suitable material, such as a metal (e.g., cobalt, cobalt alloy, etc.).

As best shown in FIGS. 6 and 8, the base 52 can be rounded and disc-shaped. The base 52 can also be concentric and symmetrical about the axis A of the extension portion 54. The base 52 can also include an inferior terminal end 55. The base 52 can be fixed to the bearing member 28 in any suitable fashion. For instance, in some embodiments, the insert 30 can be insert-molded to the bearing member 28. As such, the insert 30 can be disposed in a mold (not shown) during injection molding and formation of the bearing member 28. Also, the base 52 can include a plurality of through holes 56 spaced about the axis A. Each through hole 56 can receive the molten material of the bearing member 28 during this injection molding process to further secure the base 52 to the bearing member 28. Any air bubbles within the molten material can also be received within the through holes 56 to thereby enhance attachment between the bearing member 28 and the base 52. Furthermore, the base 52 can be surface treated to have an increased surface roughness (e.g., grit blasted) to improve adhesion of the molten material to the base 52.

Also, as shown in FIG. 2, the base 52 can be fully embedded within the bearing member 28. For instance, in some exemplary embodiments, the inferior terminal end 55 of the base 52 can be disposed superior to the inferior surface 44 of the bearing member 28, and the base 52 can also be disposed inferior from the superior surface 46 of the bearing member 28. Accordingly, the base 52 can be embedded and fixed to the bearing member 28 in a very durable and robust fashion. Also, because the insert 30 can be injection molded to the bearing member 28, manufacturing of the tibial component 14 can be facilitated.

Moreover, the extension portion 54 of the insert 30 can be substantially cylindrical. An outer surface 58 of the extension portion 54 can be exposed from the bearing member 28. The extension portion 54 can include a threaded portion 60 on the outer surface 58 thereof. Also, the extension portion 54 can include a shoulder 59 that is disposed superior to the threaded portion 60.

In addition, as shown in FIGS. 1, 2, 3A, 3B, and 5, the post 32 can be substantially boxed-shaped and can include a superior portion 61 and an inferior portion 63. The superior portion 61 can extend slightly in a posterior direction of the knee joint prosthesis 10. The post 32 can also include an anterior recess 62. Furthermore, the post 32 can include a bore 64. The bore 64 can be substantially cylindrical and can have a width corresponding to the width of the extension portion 54 of the insert 30. Moreover, the post 32 can include a counterbore 66. The counterbore 66 can be disposed on the superior portion 61 of the post 32.

The bore 64 and the counterbore 66 can receive the extension portion 54 so as to rotatably couple the post 32 to the extension portion 54 of the insert 30. As such, the post 32 can rotate about the axis A of the extension portion 54. Accordingly, as will be discussed, the post 32 can rotate to compensate for any misalignment between the tibial component 14 and the femoral component 12 of the prosthesis 10.

Figure 10A:
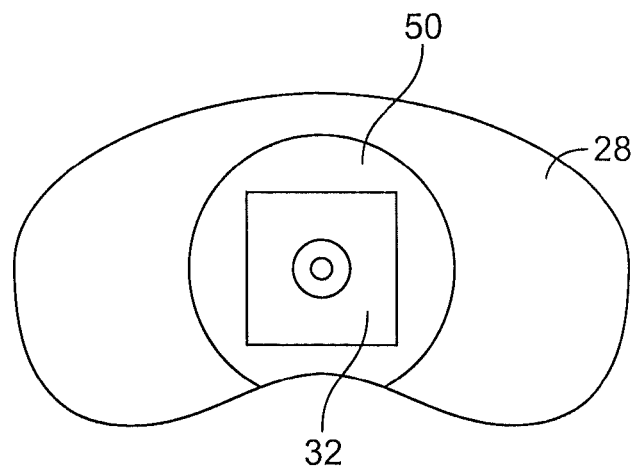
FIGS. 10A and 10B are alternative plan views of the tibial component of the knee joint prosthesis.
Figure 10B:
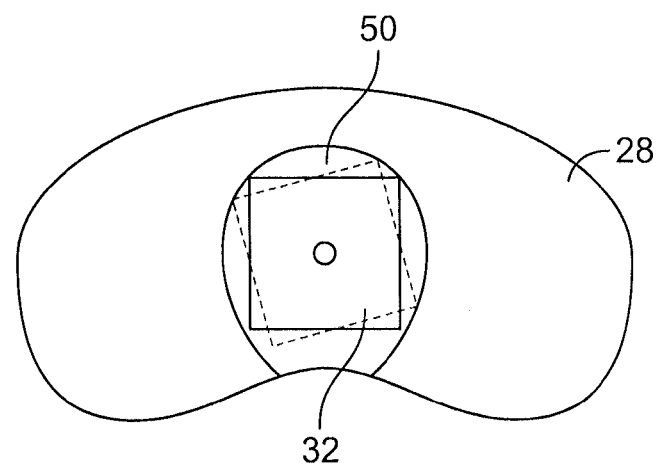

Also, the inferior portion 63 of the post 32 can be disposed within the central recess 50 of the bearing member 28. In some embodiments represented in FIG. 10A, the central recess 50 of the bearing member 28 is wide enough to allow the post 32 to rotate 360° about the axis A. However, in other embodiments represented in FIG. 10B, the central recess 50 can be shaped to abuttingly limit rotation of the post 32 about the axis A (e.g., 8° or less), as shown in phantom lines. The post 32 can be made out of any suitable material, such as a polymer (polyethylene).

Figure 9:
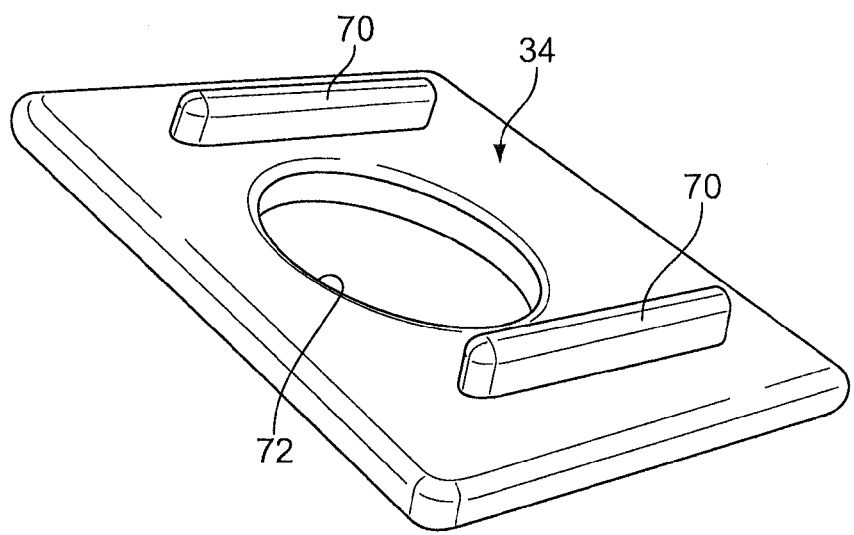
FIG. 9 is a perspective view of a washer of the knee joint prosthesis of FIG. 1.

Additionally, as shown in FIGS. 2 and 9, the washer 34 can be relatively flat and rectangular. The washer 34 can also include projections 70 (FIG. 9). The washer 34 can be fixedly coupled to the inferior portion 63 of the post 32. The washer 34 can also include a central aperture 72 that allows passage of the extension portion 54 of the insert 30. Also, as shown in FIG. 2, the washer 34 can be disposed between the post 32 and the superior surface 46 of the bearing member 28. The washer 34 can be made out of any suitable material, such as a metallic material (cobalt, cobalt alloy, etc.). As such, the washer 34 can inhibit wear of the post 32 and/or the bearing member 28 due to rotation of the post 32 relative to the bearing member 28 about the axis A.

Moreover, as shown in FIGS. 2, 3A, 3B, 7, and 8, the retention member 36 can be a nut with an internal thread 74. The retention member 36 can be received within the counterbore 66 of the post 32 to receive the extension portion 54 and threadably couple to the threaded portion 60 of the insert 30. Also, the retention member 36 can include an inner-projection 75 that abuts the shoulder 59 of the extension portion 54 to limit movement of the retention member 36 in a direction generally parallel to the axis A toward the post 32. The retention member 36 can also include a groove 76 on a superior surface 78 thereof. A separate tool (not shown) can engage with the groove 76 during implantation of the prosthesis 10 to rotate the retention member 36 about the axis A and to threadably couple the retention member 36 to the insert 30. The retention member 36 can be made out of any suitable material, such as metal (cobalt, cobalt alloy, etc.). Furthermore, the counterbore 66 of the post 32 can have a depth D (FIG. 5) that is at least equal to a length L (FIG. 7) of the retention member 36. As such, the retention member 36 can be disposed entirely within the counterbore 66.

Furthermore, the knee joint prosthesis 10 can include one or more weldments 80 (FIGS. 2, 3a, 3b, and 8). The weldments 80 can bond the retention member 36 to the insert 30 to inhibit the retention member 36 from rotating relative to the insert 30. The weldments 80 can be made in any suitable fashion, such as via a laser welding process. As such, the weldments 80 can be made at relatively low temperatures, and the materials of the other components of the knee joint prosthesis 10 are unlikely to be detrimentally affected by the welding process. Furthermore, the weldments 80 can be made without the use of any filler material, thereby facilitating implantation of the prosthesis 10.

It will be appreciated that the fixed, threaded coupling between the retention member 36 and the insert 30 can bear axial loads to limit movement of the post 32 axially away from the insert 30, and the weldments 80 can bear loads to limit rotation of the retention member 36 about the axis A relative to the insert 30. Thus, the retention member 36 can inhibit movement of the post 32 axially away from the bearing member 28. However, the post 32 can still rotate about the axis A even when the retention member 36 is fixed to the insert 30.

As shown in FIG. 1, the post 32 can be received within the opening 24 of the femoral component 12 of the knee joint prosthesis 10 and can cam against inner surfaces of the opening 24 to replicate natural motion of a knee joint. The post 32 can rotate relative to the bearing member 28 and the tibial tray 26 to thereby compensate for misalignment between the femoral component 12 and the tibial component 14 of the knee joint prosthesis 10. Thus, the knee joint prosthesis 10 can have a suitable range of motion and can closely mimic natural anatomy.

In summary, the retention member 36 can retain the post 32 on the insert 30 in a very robust manner. Also, the retention member 36 can facilitate assembly of the tibial component 14 of the knee joint prosthesis 10. Additionally, as discussed above, the insert 30 can be fixed to the bearing member 28 in a very robust manner. Furthermore, the knee joint prosthesis 10 can be relatively easy to implant and assemble. Also, the knee joint prosthesis 10 can be relatively easy to manufacture.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A knee joint prosthesis for implantation to replace a portion of a knee joint comprising:
    a tibial tray;
    a bearing member that engages the tibial tray, the bearing member including a tray engaging surface that engages the tibial tray;
    a post; and
    an insert with a base that is fixed to the bearing member and an extension portion that extends away from the bearing member and the tibial tray, the post being rotatably coupled to the extension portion to be rotatable about an axis of the extension portion and limited against movement along the axis away from the bearing member and the tibial tray, the base including an inferior terminal end that is disposed superior to the tray engaging surface of the bearing member, the base further including at least one through hole that receives the bearing member to fix the bearing member to the base.

2. The knee joint prosthesis of claim 1, wherein the base is concentric and symmetric about the axis.

3. The knee joint prosthesis of claim 1, further comprising a retention member that threadably couples to a threaded portion of the insert to limit movement of the post along the axis away from the bearing member and the tibial tray.

4. The knee joint prosthesis of claim 3, further comprising a weldment that bonds the retention member to the insert.

5. The knee joint prosthesis of claim 3, wherein the bearing member includes a polymeric material, wherein the post includes a polymeric material, wherein the tibial tray includes a metallic material, wherein the insert includes a metallic material, and wherein the retention member includes a metallic material.

6. The knee joint prosthesis of claim 1, further comprising a washer that is disposed between the post and the bearing member, the washer inhibiting wear due to rotation of the post relative to the bearing member.

7. The knee joint prosthesis of claim 1, further comprising a femoral component with an inferior portion having an opening, the inferior portion being coupled for articulation on the bearing member, the post being moveably received within the opening.

8. The knee joint prosthesis of claim 1, wherein the tibial tray is adapted to accommodate each of a cruciate retaining (CR) prosthesis, a posterior stabilized (PS) prosthesis, and a fully constrained (FC) prosthesis.

9. The knee joint prosthesis of claim 1, wherein the tibial tray has a bearing engaging surface that engages the tray engaging surface of the bearing member, the bearing engaging surface being substantially planar, the tibial tray further including a projection projects superiorly from the bearing engaging surface and that fixes the bearing member to the tibial tray.

10. A knee joint prosthesis for implantation to replace a portion of a knee joint comprising:
    a tibial component that includes:
        a tibial tray with an bearing engaging surface;
        a bearing member that is fixed to the tibial tray to be disposed adjacent the bearing engaging surface of the tibial tray, the bearing member including a tray engaging surface that engages the bearing engaging surface of the tibial tray;
        an insert with a base that is embedded within the bearing member to be fixed to the bearing member, the base including an inferior terminal end that is disposed superior to the tray engaging surface of the bearing member, the insert further including an extension portion that extends away from the bearing member and the tibial tray, the extension portion having an axis, the extension portion including a threaded portion;
        a post having a bore and a counterbore that receive the extension portion to rotatably couple the post to the extension portion for rotation about the axis relative to the insert;
        a washer that is disposed between the post and the bearing member, the washer inhibiting wear due to rotation of the post relative to the bearing member;
        a nut that receives the extension portion to threadably couple to the threaded portion of the extension portion and to limit movement of the post along the axis away from the bearing member and the tibial tray, the nut being received within the counterbore of the post; and
        a weldment that bonds the retention member to the insert; and
    a femoral component with an inferior portion having an opening, the inferior portion being coupled for articulation on the bearing member, the post being moveably received within the opening.

11. A knee joint prosthesis for implantation to replace a portion of a knee joint comprising:
    a tibial tray;

a bearing member that engages the tibial tray, the bearing member including a tray engaging surface that engages the tibial tray;

a post;

an insert with a base that is fixed to the bearing member and an extension portion that extends away from the bearing member and the tibial tray, the post being rotatably coupled to the extension portion to be rotatable about an axis of the extension portion and limited against movement along the axis away from the bearing member and the tibial tray, the base including an inferior terminal end that is disposed superior to the tray engaging surface of the bearing member; and a retention member that threadably couples to a threaded portion of the insert to limit movement of the post along the axis away from the bearing member and the tibial tray.

12. The knee joint prosthesis of claim 11, wherein the base is concentric and symmetric about the axis.

13. The knee joint prosthesis of claim 11, wherein the base includes at least one through hole that receives the bearing member to fix the bearing member to the base.

14. The knee joint prosthesis of claim 11, further comprising a weldment that bonds the retention member to the insert.

15. The knee joint prosthesis of claim 11, further comprising a washer that is disposed between the post and the bearing member, the washer inhibiting wear due to rotation of the post relative to the bearing member.

16. The knee joint prosthesis of claim 11, wherein the bearing member includes a polymeric material, wherein the post includes a polymeric material, wherein the tibial tray includes a metallic material, wherein the insert includes a metallic material, and wherein the retention member includes a metallic material.

17. The knee joint prosthesis of claim 11, further comprising a femoral component with an inferior portion having an opening, the inferior portion being coupled for articulation on the bearing member, the post being moveably received within the opening.

18. The knee joint prosthesis of claim 11, wherein the tibial tray is adapted to accommodate each of a cruciate retaining (CR) prosthesis, a posterior stabilized (PS) prosthesis, and a fully constrained (FC) prosthesis.

19. The knee joint prosthesis of claim 11, wherein the tibial tray has a bearing engaging surface that engages the tray engaging surface of the bearing member, the bearing engaging surface being substantially planar, the tibial tray further including a projection projects superiorly from the bearing engaging surface and that fixes the bearing member to the tibial tray.

* * * * *

UNITED STATES PATENT AND TRADEMARK OFFICE
CERTIFICATE OF CORRECTION

Page 1 of 1

PATENT NO.         : 8,152,853 B2
APPLICATION NO.    : 12/479148
DATED              : April 10, 2012
INVENTOR(S)        : Nathan E. Belcher It is certified that error appears in the above-identified patent and that said Letters Patent is hereby corrected as shown below:

In the Specification

Column 2, Line 43; After "an" delete "insert".
Column 3, Line 2; After "according" insert --to--.
Column 6, Line 61; "(FIGS. 2, 3a, 3b, and 8)" should be
--(FIGS. 2, 3A, 3B and 8)--.

In the Claims

Column 8, Line 33, Claim 10; "an bearing" should be --a bearing--.

Signed and Sealed this
Thirteenth Day of May, 2014

Michelle K. Lee
*Deputy Director of the United States Patent and Trademark Office*